United States Patent [19]

Jessop

[11] 4,269,803
[45] May 26, 1981

[54] SLIDE TRANSFER MECHANISM

[75] Inventor: Thomas C. Jessop, Webster, N.Y.

[73] Assignee: Eastman Kodak Company, Rochester, N.Y.

[21] Appl. No.: 54,063

[22] Filed: Jul. 2, 1979

[51] Int. Cl.³ .................... G01N 21/01; G01N 35/04
[52] U.S. Cl. ...................................... 422/63; 422/57; 422/58; 422/65
[58] Field of Search .................. 422/63, 64, 65, 66, 422/67; 141/130

[56] References Cited

U.S. PATENT DOCUMENTS

| | | |
|---|---|---|
| 3,057,516 | 10/1962 | Gentile et al. . |
| 3,263,078 | 7/1966 | Thackara et al. . |
| 3,580,685 | 5/1971 | Eriksson ............................ 356/244 |
| 3,650,437 | 3/1972 | Binnings et al. ...................... 222/136 |
| 3,659,934 | 5/1972 | Costanza et al. . |
| 3,918,910 | 11/1975 | Soya et al. . |
| 3,992,158 | 11/1976 | Przybylowicz et al. .............. 422/57 |
| 4,053,381 | 10/1977 | Hamblen et al. ................ 204/195 M |
| 4,056,358 | 11/1977 | Priarone et al. . |
| 4,110,167 | 8/1978 | Melnyk . |
| 4,152,390 | 5/1979 | Nosco et al. . |

FOREIGN PATENT DOCUMENTS 50-31736 9/1975 Japan .

Primary Examiner—Ronald Serwin
Attorney, Agent, or Firm—D. D. Schaper

[57] ABSTRACT

A slide transfer mechanism is disclosed for advancing an analysis slide through a plurality of work stations in a chemical analyzer. The transfer mechanism comprises a pair of slidable members which are movable together to advance slides in each of the stations and are movable independently of each other to advance slides in less than all of the stations. The slides are releasably held by spring means in each of the work stations.

15 Claims, 5 Drawing Figures

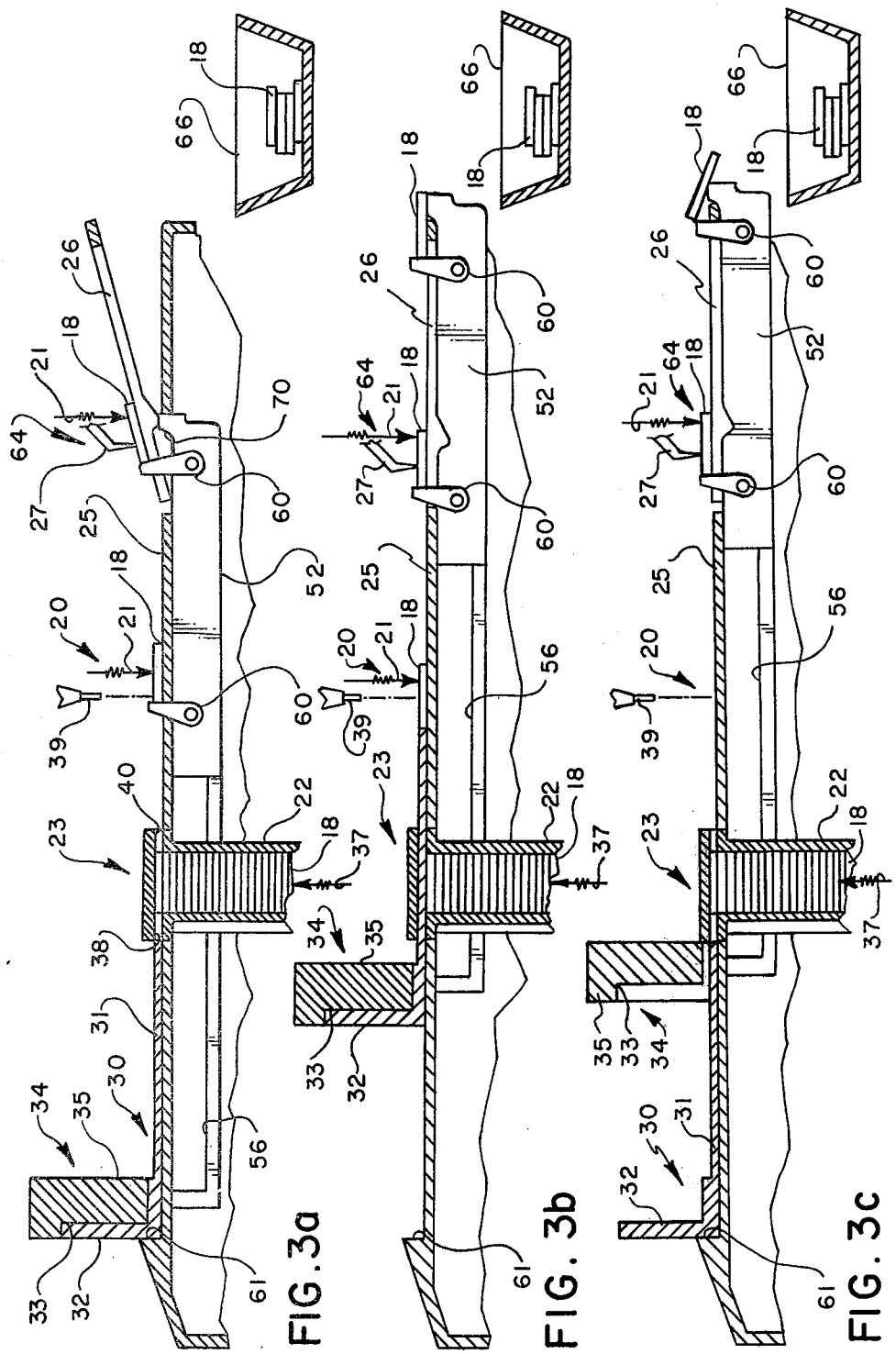

SLIDE TRANSFER MECHANISM

CROSS-REFERENCE TO RELATED APPLICATIONS

Reference is made to commonly-assigned U.S. patent application Ser. No. 927,702, entitled CHEMICAL ANALYZER, filed in the name of Schnipelsky et al., on July 24, 1978.

BACKGROUND OF THE INVENTION (1) Field of the Invention

This invention relates to apparatus for the chemical analysis of substances, and more particularly, to a mechanism for advancing an analysis slide through a plurality of work stations in a chemical analyzer.

(2) State of the Prior Art

Recent developments have provided analysis slides for use in performing quantitative analyses of biological fluids. The slides are essentially planar, contain reagents in a dry form, and can be loaded into a cartridge for use in a chemical analyzer. In the operation of such an analyzer, an analysis slide is fed from a cartridge into a metering station where a predetermined amount of fluid is deposited on the analysis slide. After an appropriate incubation period, the slide is moved to an analysis station where a change in the slide is sensed, the amount of change being proportional to a particular analyte in the sample fluid. The slide is used only once and is discarded after the reading has been taken. An analyzer for use with slides of this type is described in commonly-assigned U.S. Pat. No. 4,152,390, granted on May 1, 1979.

Apparatus for use with analysis slides of the type described above can be made relatively small, and in some cases portable, since no liquid reagents are used which require intricate solution handling and transport capabilities. In small apparatus of this type, certain advantages result from providing simple, manually-operated mechanisms for advancing analysis slides from station to station. An example of such a slide transfer mechanism is shown in the aforesaid U.S. patent application Ser. No. 927,702, in which a single elongate member, mounted for slidable movement, is used to advance an analysis slide along a track which extends through each station of the analyzer. Such a transfer mechanism works well with a low-capacity analyzer. However, each slide must be manually inserted in the track, and thus, the mechanism is not suitable for use in semi-automatic analyzers where a relatively high throughput is desired.

The U.S. Pat. No. 4,110,167, to Melnyk, granted on Aug. 29, 1978, discloses a "semi-automated" slide processor device in which a slide bar is manually actuated to advance slides through the device. The slide bar is adapted to advance slides by pushing new slides from a slide supply into engagement with slides being processed in the device. Such a method of moving slides can cause undesirable agitation of fluids carried on the slides; further, there is no way to clear the device of slides, since new slides must be used to advance the processed slides. Slides left in the apparatus between runs are subject to contamination which can, of course, affect the test results.

OBJECTS OF THE INVENTION

It is an object of the invention to overcome the above-described problems of prior art devices and to provide a novel and improved slide transfer means for advancing analysis slides through an analyzer.

Another object of the invention is to provide apparatus of the type described in which a slide transfer mechanism includes a pair of members which can be actuated together to advance slides in each of the work stations in an analyzer or actuated independently of each other to advance slides in less than all of the work stations.

Still another object of the invention is to provide a slide transfer mechanism in an analyzer which will transport analysis slides with a minimum of agitation of the fluids contained on the slides.

A further object of the invention is to provide a manually-actuated slide transfer mechanism which is adapted to selectively advance analysis slides in an analyzer.

Other objects and advantages will become apparent from the following summary and description of the preferred embodiment, when considered in the light of the attached drawings.

SUMMARY OF THE INVENTION

This invention relates to apparatus for the chemical analysis of biological fluids in which the fluid is metered onto a generally planar, dry analysis slide which is analyzed after an appropriate period of incubation.

More specifically, in accordance with one aspect of the invention, there is provided a transfer means for advancing an analysis slide through a plurality of work stations in a chemical analyzer. The transfer means is adapted to advance the slide along a path extending through each of the stations and comprises a first member for advancing a slide from a first station to a second station and a second member for indexing the slide from the second station to a third station, the members being movable together to advance slides in each of the stations when a force is applied to the first member, and the second member being movable independently of the first member to advance slides in less than all of the stations when a force is applied to the second member.

In a preferred embodiment of the invention, the transfer means includes a pair of members which are slidably mounted in the apparatus. A slide advance member is adapted to remove an analysis slide from a cartridge of slides and deposit the slide at a metering station. After a predetermined amount of fluid has been deposited on the slide, an indexer member is adapted to transport the slide to an analysis station. The indexer member comprises a pair of fingers for simultaneously moving a pair of slides. The fingers are pivotally mounted and are spring biased against a stop such that the fingers are held in a position to advance slides when the indexer member is moved in a slide advance direction, and the fingers are adapted to pivot under the slides when the indexer member is returned to its starting position. The slide advance and indexer members are mounted such that a force applied to the slide advance member will move both of the members together to advance slides in each of the work stations, and a force applied to the indexer member will only move slides in contact with the indexer member.

BRIEF DESCRIPTION OF THE DRAWINGS

FIGS. 3a–3c show the relative positions of the slide advance and indexer members in various modes of operation.

DESCRIPTION OF THE PREFERRED EMBODIMENT

The invention is described hereinafter in connection with an analyzer for performing quantitative chemical analyses of biological fluids, such as blood serum. However, the invention is not so limited, and it can also be employed in other types of apparatus where objects must be transferred from station to station and accurately located in each of the stations.

The invention is particularly useful with potentiometric analyzers in which case the substrate which makes the test possible comprises a pair of electrodes selective to the ion activity of choice. Recent developments have provided the electrodes in essentially planar, dry form suitable for use in pairs in an analyzer. An example of such an analyzer is described and claimed in the aforesaid U.S. patent application Ser. No. 927,702, entitled CHEMICAL ANALYZER. The invention can also be employed in an analyzer using a radiometric detector which will read a suitable substrate incorporating, for example, reagents that create a dye in proportion to the analyte being measured. An analyzer of this type is disclosed in the aforesaid U.S. Pat. No. 4,152,390.

One form of test element which is suitable for use in the apparatus of the subject invention is disclosed in the patent to Hamblen et al., U.S. Pat. No. 4,053,381, granted on Oct. 11, 1977. This patent describes a test element, or analysis slide, of the type which is used to potentiometrically designate the activity of ions in a liquid test solution.

The invention can also be used with other forms of test elements, as for example, the element disclosed in the commonly-owned U.S. Patent to Przybylowicz et al., U.S. Pat. No. 3,992,158, granted on Nov. 16, 1976. The test element disclosed in this patent is formed as a multi-layered element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Figure 1:
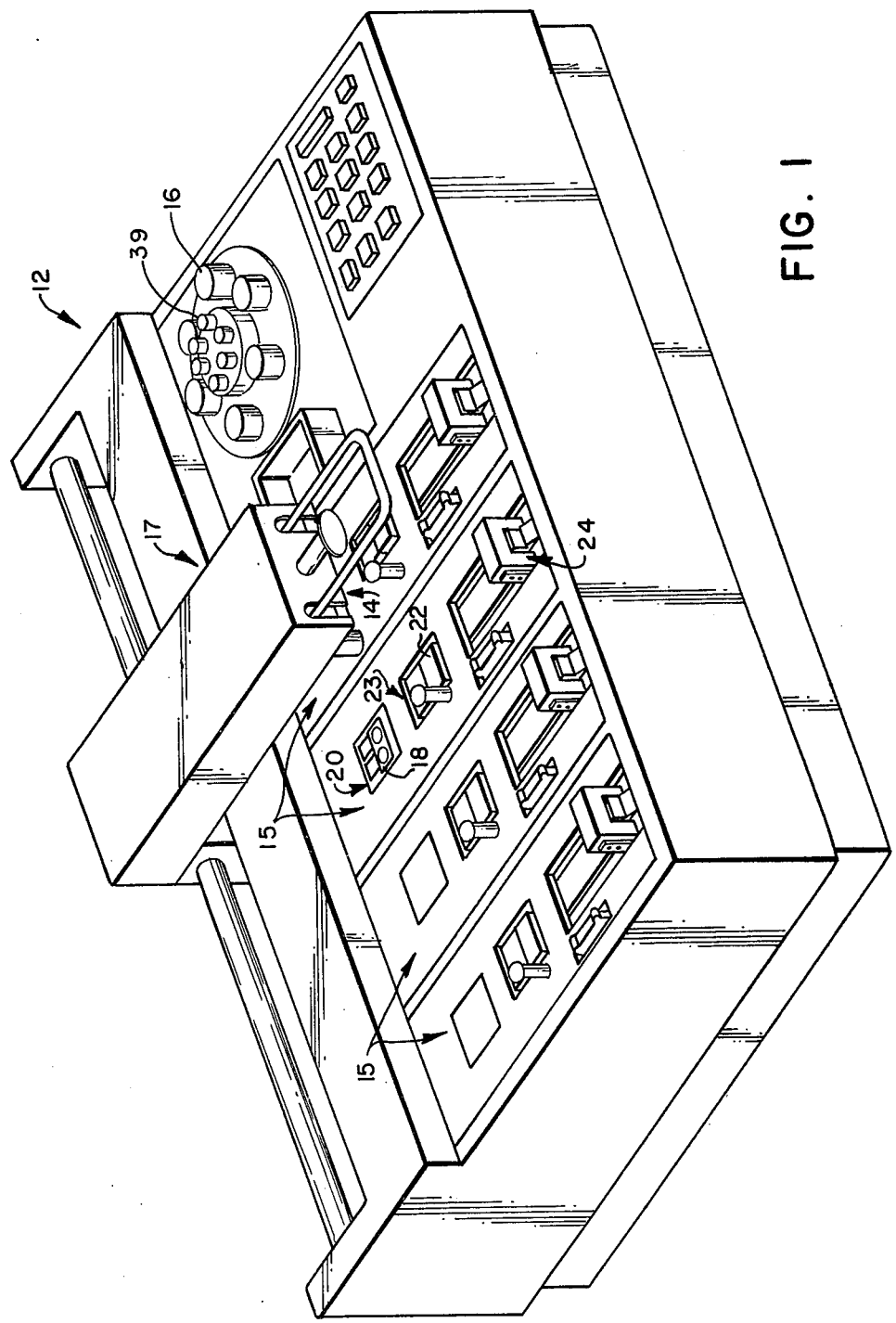
FIG. 1 is a perspective view of a chemical analyzer of the type which is adapted to employ the slide transfer mechanism described herein.

In accordance with a preferred embodiment of the invention, there is shown in FIG. 1 a potenmetric analyzer 12 of a type which is adapted to employ a slide transfer mechanism as described herein. Analyzer 12 comprises four channels 15 for simultaneously performing four different analyses; operation in each of the channels is generally similar, and thus, the operation of only one channel will be described. Sample fluids are supplied to the analyzer in sample cups 16. A metering device 14 is movable on a carriage 17 to a cup 16 where it aspirates a supply of sample fluid sufficient for the number of tests to be performed. Device 14 is then moved to a metering station 20 in one of the channels 15 where it deposits a drop of sample fluid along with a drop of reference fluid on an analysis slide 18.

Figure 2:
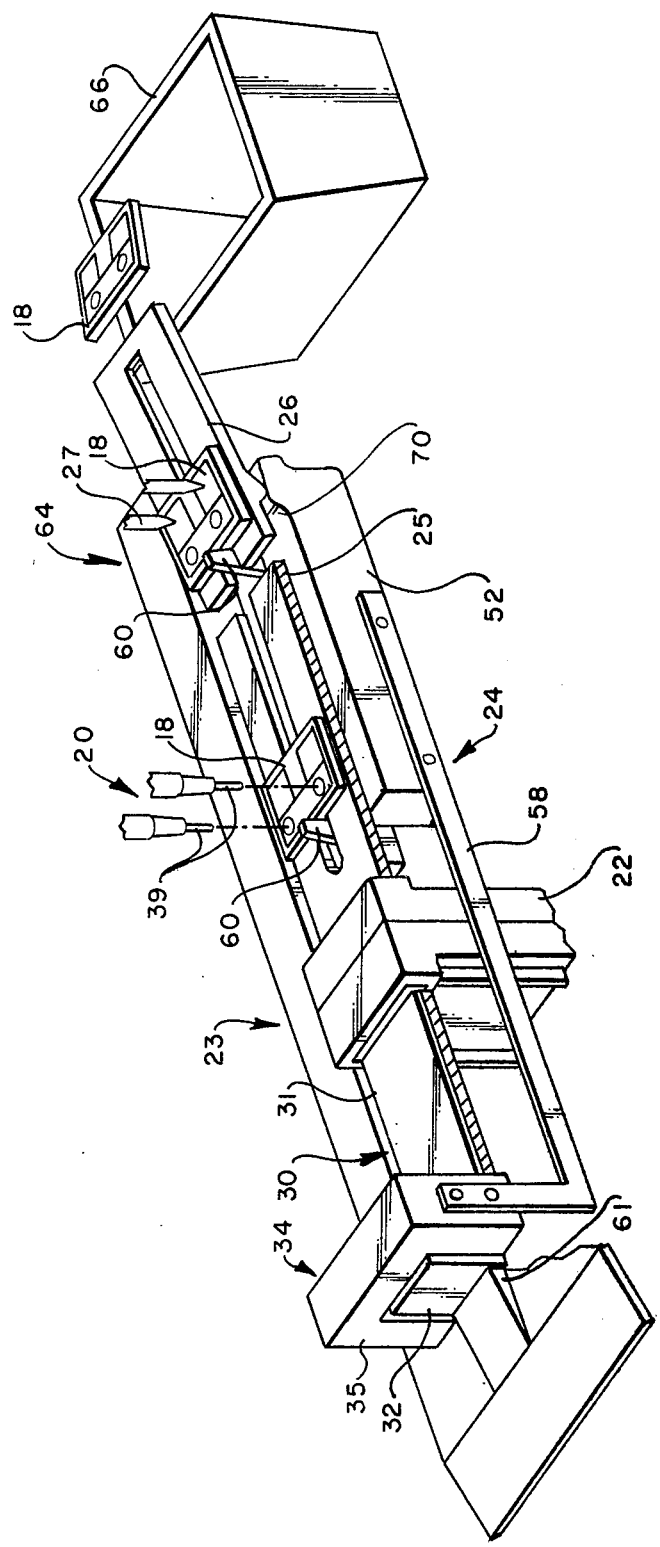
FIG. 2 is a perspective view of the slide transfer mechanism of the subject invention.

Analysis slides 18 are supplied to analyzer 12 in a cartridge 22 which is received at a reagent supply station 23. Slides 18 are removed from cartridge 22, located adjacent the forward end of analyzer 12, and moved rearwardly into metering station 20 by a slide transfer mechanism 24, as will be explained in more detail hereinafter. After fluids have been deposited on analysis slide 18, the slide is moved from metering station 20 into an analysis station 64 located at the rear of analyzer 12 (FIG. 2). In analysis station 64, slide 18 is moved into engagement with contacts 27 of an electrometer, not shown, to measure the potential developed across the ion-selective electrodes. Slides 18 are releasably held in the metering station 20 and analysis station 64 by a spring means 21, shown schematically in FIGS. 3a and 3b.

Slide transfer mechanism 24, as shown in FIG. 2, provides a means for advancing an analysis slide 18 along a path, formed by a track 25 and a track extension 26, which passes through each of the work stations of analyzer 12. Transfer mechanism 24 comprises a slide advance member 30 which is adapted to deliver a slide 18 to metering station 20, and an indexer member 34 which advances slide 18 through successive stations on the analyzer.

Slide advance member 30 is generally L-shaped and includes a blade 31, which is slidably mounted for reciprocative movement on track 25, and a tab 32 which can be grasped by the operator. As shown in FIGS. 3a–3c, blade 31 of advance member 30 is adapted to enter cartridge 22 through a slot 38. The uppermost slide 18 in cartridge 22 is positioned, for contact by member 30, by means of a spring pusher rod 37, indicated schematically in FIGS. 3a–3c. As slide member 30 is moved rearwardly into contact with a slide 18, it forces the slide out through an exit slot 40 in cartridge 22 and delivers the slide to metering station 20 where the slide is in a position to receive fluid from metering tips 39. Member 30 extends under a handle 35 of member 34, and tab 32 is adapted to be received in a recess 33 in handle 35. As will be apparent hereinafter, a force directed against tab 32 will move both member 30 and member 34 to advance slides in each of the analyzer stations.

Indexer member 34 comprises a shuttle block 52 which is slidably mounted in analyzer 12 and is connected to handle 35 by side pieces 56, 58. Pivotally mounted on block 52 are a pair of fingers 60 which are arranged in tandem and are spaced apart a distance generally equal to the distance between the analysis station 64 and the metering station 20. Fingers 60 are biased in a counterclockwise direction, as viewed in FIG. 3a, by springs, not shown; and the fingers are normally held by the springs in an upright position (FIG. 3a). The fingers 60 remain in the upright position during a slide advance stroke, that is during the movement of indexer member 34 toward the rear end of analyzer 12. Fingers 60 can pivot in a clockwise direction, as viewed in FIGS. 3a, against spring pressure to move under slides 18 on the return stroke, that is during movement of indexer member 34 toward the forward end of analyzer 12. A cam surface 70 on block 52 is adapted to elevate track extension 26 on the return stroke of block 52 to bring slide 18 into engagement with contacts 27. At the completion of the return stroke of indexer member 34, member 34 is moved to a fully retracted position in which advance member 30 is in contact with a stop 61, as shown in FIG. 3a.

Operation of Applicant's invention can best be shown by reference to FIGS. 3a–3c. After a cartridge 22 containing slides for a desired test has been installed on analyzer 12, a force is directed against tab 32 on slide advance member 30 to advance a slide to metering station 20. When a predetermined quantity of reference fluid and sample fluid has been deposited on slide 18, indexer member 34 and slide advance member 30 are moved together to advance the slide 18 in the metering station 20 and to deliver a new slide 18 to metering station 20. Thus, after the first two steps just described, slides will be in reagent supply station 23, metering station 20 and analysis station 64, as shown in FIG. 3a.

After a reading has been taken on the slide 18 in analysis station 64, slides are advanced at each of the stations by movement of both the slide advance member 30 and the indexer member 34. (See FIG. 3b.) Movement of slide advance member 30 and indexer member 34 together can be accomplished by applying a force against tab 32 of slide advance member 30. When a slide is moved out of analysis station 64 by indexer member 34, the slide is deposited in a waste receptacle 66.

It is possible to clear analyzer 12 of slides 18 by moving only the indexer member 34, as shown in FIG. 3c; this step would be performed, for example, at the end of a day's run. It can be seen that to completely clear the analyzer will require two complete cycles of indexer member 34.

Slide transfer mechanism 24 provides a simple and efficient means for manually advancing slides in an analyzer and for precisely positioning the slides in the analyzer work stations. Since the slides are moved by contact with fingers 60 of the transfer mechanism, rather than by pushing one slide against another, the slides are advanced through the analyzer with a minimum of agitation. If only one test is desired, the operator can advance a single slide through the analyzer. If continuous testing is required, the operator can maintain slides at each of the analyzer stations to achieve the maximum throughput. When testing has been completed, the indexer member can be employed to remove processed slides from the analzyer.

The invention has been described in detail with particular reference to preferred embodiments thereof, but it will be understood that variations and modifications can be effected within the spirit and scope of the invention.

What is claimed is:

1. In an apparatus for chemical analysis of a sample fluid wherein operations are performed on an analysis slide at a plurality of stations in the apparatus, the combination comprising:
    means defining a path for movement of a slide between and through said stations; and
    transfer means for advancing a slide along said path, said transfer means comprising a first member for advancing a slide from a first station to a second station and a second member for indexing the slide from said second station to a third station, said members being movable together to advance slides in each of said stations when a force is applied to said first member, and said second member being movable independently of said first member to advance slides in less than all of said stations when a force is applied to said second member.

2. The combination, as defined in claim 1, wherein said members are slidably mounted and said members are adapted to advance a slide from a forward end of the apparatus toward a rear end thereof.

3. The combination, as defined in claim 2, wherein said apparatus comprises a reagent supply station, a metering station and an analysis station, said apparatus is adapted to receive a supply of slides at said reagent supply station, said first member is adapted to move a slide from said supply into said metering station, and said second member is adapted to deliver the slide from said metering station to said analysis station and to effect the removal of the slide from the analysis station.

4. The combination, as defined in claim 3, wherein each of said stations comprises restraining means which is adapted to releasably hold a slide in the station, and said second member comprises pivotally mounted fingers which are adapted to engage and move a slide toward said rear end and to be pivoted under a slide held by said restraining means in movement toward said forward end.

5. The combination, as defined in claim 4, wherein the fingers are arranged in tandem on said second member, and the distance between said fingers is generally equal to the distance between said metering station and said analysis station.

6. The combination, as defined in claim 2, wherein said second member comprises a recessed portion for receiving said first member, and said second member is movable by said first member when the first member is in engagement with said recessed portion.

7. Apparatus for measuring a characteristic of a sample fluid wherein the fluid is deposited on an analysis slide which is analyzed after an appropriate period of time, said apparatus comprising:
    means defining a path for movement of an analysis slide in said apparatus;
    a plurality of apparatus elements, said elements being arranged along said path to interact with the slide in a preselected sequence, said elements including metering means for depositing a predetermined quantity of fluid on a slide located on said path and analysis means for sensing a characteristic of the slide after an appropriate period of time; and
    slide transfer means for sequentially applying a force to a slide supported on said path to advance the slide past said elements, said slide transfer means comprising a first member for moving a slide to said metering means and a second member for moving the slide from said metering means to said analysis means, and said members being movable together when a force in the direction of slide advancement is applied to said first member and relative to each other when a force is applied to said second member in said direction of slide advancement.

8. Apparatus, as defined in claim 7, wherein said apparatus is adapted to receive a slide supply means, and said first member is adapted to remove a slide from said slide supply means and deliver the slide to said metering means.

9. Apparatus, as defined in claim 7, wherein said slide path is formed by a generally linear track, and said first member is slidably mounted on said track.

10. Apparatus, as defined in claim 9, wherein said analysis means comprises contact means, and said second member comprises means for moving a slide into engagement with said contact means.

11. A slide transfer mechanism for use in a chemical analyzer of the type in which a fluid is metered onto an analysis slide which is analyzed after an appropriate period of time, said slide transfer mechanism comprising:
    a plurality of members mounted for reciprocative movement, said members being adapted to engage a slide in a predetermined sequence to advance the slide through a plurality of stations in said analyzer, one of said members being engageable with a second member to move said second member when a force is applied to said one member, and said second member being movable independently of said first member when a force is applied thereto; and means for releasably engaging said slides at said stations to prevent movement of the slide in a direction opposite to the direction of slide advancement.

12. A slide transfer mechanism, as defined in claim 11, wherein said analyzer includes a reagent supply station, a metering station and an analysis station, said one member is adapted to feed a slide from the supply station into the metering station, and said second member is adapted to move the slide from said metering station to the analysis station.

13. A slide transfer mechanism as defined in claim 11, wherein said second member comprises pivotally mounted fingers which drivingly engage a slide when said second member is moving in the direction of slide advancement and which are movable relative to the slide when moving in a direction opposite to the direction of slide advancement.

14. A slide transfer mechanism, as defined in claim 11, wherein said second member comprises a handle having a recessed portion therein, and said one member comprises a tab receivable in said recessed portion.

15. A slide transfer mechanism, as defined in claim 14, wherein said handle and said tab are adapted to be grasped by an operator for manual actuation of said mechanism.

* * * * *